United States Patent [19]
Ptashne et al.

[11] 4,332,892
[45] Jun. 1, 1982

[54] PROTEIN SYNTHESIS

[75] Inventors: Mark Ptashne; Gail D. Lauer; Thomas M. Roberts, all of Cambridge, Mass.; Keith C. Backman, San Francisco, Calif.

[73] Assignee: President and Fellows of Harvard College, Cambridge, Mass.

[21] Appl. No.: 111,101

[22] Filed: Jan. 10, 1980

Related U.S. Application Data

[63] Continuation of Ser. No. 3,102, Jan. 15, 1979, abandoned.

[51] Int. Cl.$^3$ ............................................. C12P 21/00
[52] U.S. Cl. ...................................... 435/68; 435/70; 435/172
[58] Field of Search ...................... 435/172, 70, 71, 68

[56] References Cited
PUBLICATIONS

Chang et al., Nature, vol. 275, pp. 617–624, Oct. 19, 1978.
Itakura et al., Science, vol. 198, pp. 1056–1063 (1977).
Backman et al., Proc. Natl. Acad. Sci., USA, vol. 73, pp. 4174–4178 (1976).
Backman et al., Cell, vol. 13, pp. 65–71, Jan. 1978.

*Primary Examiner*—Alvin E. Tanenholtz

[57] ABSTRACT

This invention is a process to produce specific proteins coded for by eukaryotic (or prokaryotic) DNA in bacteria. The invention, which uses recombinant DNA techniques, produces proteins in their natural, functional state unencumbered by extraneous peptides.

6 Claims, No Drawings

PROTEIN SYNTHESIS

This is a continuation of application Ser. No. 3,102, filed Jan. 15, 1979, and now abandoned.

The invention described herein was made in the course of work under a grant or award from the National Science Foundation.

This invention is a method for producing in bacteria prokaryotic or eukaryotic proteins in native, unfused form free from extraneous peptides.

Recombinant DNA techniques in vitro have been used to insert a variety of eukaryotic genes into plasmids carried by *Escherichia coli* in an effort to induce these bacteria to produce eukaryotic proteins. Most of these genes have not directed the synthesis of the native proteins because the eukaryotic signals coding for initiation of transcription and/or translation do not function well in *E. coli*. One proposed solution to this problem has been the fusion of the eukaryotic gene with a bacterial gene. The process results in the production of a hybrid protein, a portion of which at its carboxyl terminus is constituted by the eukaryotic protein. In one case, it has been possible to separate a small biologically active protein from a fusion product (Itakura, K. et al., *Science* 198, 1056 (1977)).

Gene expression takes place by transcription into mRNA then translation into protein. To do these operations, the DNA preceding the gene must have a sequence which: (a) directs efficient binding of bacterial RNA polymerase and efficient initiation of transcription, and (b) codes for a mRNA that directs efficient binding of mRNA to the ribosomes and initiation of translation into protein.

The present invention provides a method of producing native, unfused prokaryotic or eukaryotic protein in bacteria which comprises inserting into a bacterial plasmid a gene for a prokaryotic or eukaryotic protein and a portable promoter consisting of a DNA fragment containing a transcription initiation site recognized by RNA polymerase and containing no protein translational start site, said promoter being inserted ahead of a protein translational start site of said gene to form a fused gene having a hybrid ribosome binding site, inserting said plasmid into said bacteria to transform said bacteria with said plasmid containing said fused gene, and culturing the transformed bacteria to produce said prokaryotic or eukaryotic protein.

The present invention utilizes nucleases, restriction enzymes, and DNA ligase to position a portable promoter consisting of a DNA fragment containing a transcription site but no translation initiation site near the beginning of the gene which codes for the desired protein to form a hybrid ribosomal binding site. The protein produced by the bacterium from this hybrid is the native derivative of the implanted gene. It has been found that the endonuclease digestion product of the *E. coli lac* operon, a fragment of DNA which contains a transcription initiation site but no translational start site, has the required properties to function as a portable promoter in the present invention, being transcribed at high efficiency by bacterial RNA polymerase. The mRNA produced contains a Shine-Dalgarno (S-D) Sequence but it does not include the AUG or GUG required for translational initiation. However, in accordance with the present invention, a hybrid ribosomal binding site is formed consisting of the S-D sequence and initiator from the lac operon and the ATG sequence of the gene, and such a fused gene is translated and transcribed efficiently. Using the enzymes exonuclease III and S1, the promoter may be put at any desired position in front of the translational start site of the gene in order to obtain optimum production of protein. Since the promoter can be inserted at a restriction site ahead of the translational start site of the gene, the gene can first be cut at the restriction site, the desired number of base pairs and any single stranded tails can be removed by treating with nucleases for the appropriate time period, and religating.

The following specific example is intended to illustrate more fully the nature of the present invention without acting as a limitation upon its scope.

EXAMPLE

A rabbit β-globin gene was first cloned into the Hin III site of pBR322, a plasmid of the *E. coli* bacteria, via restriction enzyme cuts of the initial DNA, reconstitution of the gene by T4 ligase, insertion of the reconstituted gene into the Hin III site using chemically synthesized Hin III linkers, and religating with DNA ligase.

The Hin III cut at the carboxyl end of the cloned gene was removed by partially digesting with Hin III, filling in the resulting Hin III "sticky ends" with *E. coli* DNA polymerase I, and religating with T4 ligase. This left in the resulting plasmid a single Hin III cut 25 base pairs ahead of the amino terminus of the globin gene.

Differing number of the 25 base pairs between the Hin III cut and the ATG signalling the start point of translation were removed from different samples of the cloned gene as follows: the plasmid was cut with Hin III, resected for various times from 0.5 to 10 minutes with Exo III, then treated with S1 to remove single-stranded tails.

The portable promoter of the lac operon, an R1-Alu restriction fragment of *E. coli* DNA, was then inserted by treating each sample of the plasmid with R1 which cuts at a unique site some 30 base pairs upstream from the Hin III site, and the portable promoter was inserted into the plasmid backbone at this site. This requires one "sticky end" and one "flush" end, both of which are ligated by the same treatment with ligase.

Colonies of *E. coli* each containing one of these resulting plasmids were then screened for β-globin production using RIA-screening techniques to identify the one or more producing β-globin.

The globin gene in the above construction can be any gene coding for prokaryotic or eukaryotic proteins, and any other unique restriction site can be employed in place of the Hin III site. If the restriction site is located inconveniently far from the beginning of the gene, it may be moved (for example, a Hin III site may be moved by opening the plasmid with Hin III, digesting with Exo III and S1, then religating the resulting plasmid in the presence of excess Hin III linkers). Any suitable restriction site can be employed for insertion of the portable promoter in place of the R1 site (e.g. Pst, BAM, or Sal I). Finally, it should be emphasized that the most difficult step, the cloning of the gene into the plasmid, is done once and left unchanged. The promoter fragment will confer its constitutive expression on the cell so it is easy to screen for the intact promoters.

What is claimed is:

1. The method of producing native, unfused prokaryotic or eukaryotic protein in bacteria which comprises inserting into a bacterial plasmid a gene for a prokaryotic or eukaryotic protein and a portable promoter consisting of a DNA fragment containing a Shine-Dalgarno sequence and a transcription initiation site recognized by RNA polymerase and containing no protein translational start site, said promoter being inserted upstream from a protein ATG translational start site of said gene, at a position to obtain production of said protein, to form a fused gene having said Shine-Dalgarno sequence, said transcription initiation site, and the ATG signalling the start point of translation, inserting said plasmid into said bacteria to transform said bacteria with said plasmid containing said fused gene, and culturing the transformed bacteria to produce said unfused prokaryotic or eukaryotic protein.

2. The method as claimed in claim 1 in which said bacteria is *E. coli*.

3. The method as claimed in claims 1 or 2 in which said portable promoter is the product of restriction endonuclease digestion of an operon.

4. The method claimed in claim 2 in which said portable promoter is the product of restriction endonuclease digestion of the lac operon of *E. coli*.

5. The method as claimed in claims 1 or 2 in which said gene insertion comprises cloning said gene into said plasmid, adjusting the spacing between said inserted gene and a preceding unique restriction site by treating with a nuclease, and cloning said portable promoter into said restriction site.

6. The method as claimed in claim 2 in which said gene insertion comprises cloning said gene into said plasmid, adjusting the spacing between said gene and a preceding unique restriction site by treating with a nuclease, and cloning into said restriction site a portable promoter formed by the endonuclease digestion of the lac operon of *E. coli*.

* * * * *

UNITED STATES PATENT AND TRADEMARK OFFICE
CERTIFICATE OF CORRECTION

PATENT NO. : 4,332,892
DATED : June 1, 1982
INVENTOR(S) : Mark Ptashne et al.

It is certified that error appears in the above-identified patent and that said Letters Patent are hereby corrected as shown below:

Under "Inventors", delete the following names:

"Gail D. Lauer; Thomas M. Roberts"

Signed and Sealed this

Fourteenth Day of September 1982

[SEAL]

Attest:

GERALD J. MOSSINGHOFF

*Attesting Officer*  *Commissioner of Patents and Trademarks*